(12) United States Patent
Wohleb

(10) Patent No.: US 7,087,437 B2
(45) Date of Patent: Aug. 8, 2006

(54) DIRECT VIAL SURFACE SORBENT MICRO EXTRACTION DEVICE AND METHOD

(75) Inventor: Robert H. Wohleb, Gig Harbor, WA (US)

(73) Assignee: VICI Gig Harbor Group, Inc., Gig Harbor, WA (US)

( * ) Notice: Subject to any disclaimer, the term of this patent is extended or adjusted under 35 U.S.C. 154(b) by 378 days.

(21) Appl. No.: 10/663,955

(22) Filed: Sep. 16, 2003

(65) Prior Publication Data

US 2005/0059162 A1    Mar. 17, 2005

(51) Int. Cl.
*G01N 30/00*    (2006.01)

(52) U.S. Cl. .................. 436/178; 215/227; 422/69; 422/101; 422/102

(58) Field of Classification Search ........... 422/69, 422/70, 89, 101, 102; 436/161, 162, 175, 436/178, 181; 210/660, 662; 95/89, 90; 96/105; 215/227
See application file for complete search history.

(56) References Cited

U.S. PATENT DOCUMENTS

| | | | |
|---|---|---|---|
| 3,958,944 A * | 5/1976 | Wong ..................... 422/72 |
| 4,382,000 A * | 5/1983 | Wisebaker et al. ........ 210/638 |
| 4,720,351 A * | 1/1988 | Flynn et al. ............. 510/277 |
| 5,279,742 A | 1/1994 | Markel et al. |
| 5,391,298 A | 2/1995 | Pieper et al. |
| 5,403,489 A | 4/1995 | Hagen et al. |
| 5,415,779 A | 5/1995 | Markell et al. |
| 5,472,600 A | 12/1995 | Ellefson et al. |
| 5,565,622 A | 10/1996 | Murphy |
| 5,595,649 A | 1/1997 | Markell et al. |
| 5,595,653 A | 1/1997 | Good et al. |
| 5,635,060 A | 6/1997 | Hagen et al. |
| 5,691,206 A | 11/1997 | Pawliszyn |
| 5,897,779 A | 4/1999 | Wisted et al. |
| 5,911,883 A | 6/1999 | Anderson |
| 5,947,274 A * | 9/1999 | Taskis et al. .............. 206/204 |
| RE36,811 E | 8/2000 | Markel et al. |
| 6,287,521 B1 * | 9/2001 | Quay et al. .............. 422/101 |
| 2002/0150923 A1 | 10/2002 | Malik |

* cited by examiner

*Primary Examiner*—Jan M. Ludlow
(74) *Attorney, Agent, or Firm*—Crain, Caton & James, P.C.; James E. Hudson, III

(57) ABSTRACT

A device for extracting an analyte from a sample matrix comprises a sorption vial with a conically shaped interior surface, which is coated with a sorbent material. A method for extracting an analyte from a sample matrix includes retaining the sorption vial within a sample vessel with the sorbent coating exposed to the sample matrix contained in the sample vessel. After the analyte is collected in the sorbent material, the sorption vial may be removed from the sample vessel and sealed, or a small amount of elution solvent may be added to the sorption vial before sealing. The sorption vial containing the analyte may then be stored or transported to a lab for further analysis.

22 Claims, 4 Drawing Sheets

US 7,087,437 B2

DIRECT VIAL SURFACE SORBENT MICRO EXTRACTION DEVICE AND METHOD

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

This invention relates to the extraction and collection of one or more analytes by a sorption process. Specifically, this invention relates to a device and method for performing direct vial extraction.

2. Description of the Related Art

To prepare samples for chemical analysis, often analytes, or the compound of interest, must be separated from a sample matrix, such as water, soil or animal tissue and presented in a form suitable for a particular piece of analytical equipment, such as a gas or liquid chromatograph. There are various extraction methods known and used to collect and prepare samples for such chemical analysis. These methods include liquid/liquid extraction, solid phase extraction, solid phase microextraction and stir-bar sorptive extraction. The trend in the industry is toward simplified sample preparation that results in pollution prevention and waste minimization.

Liquid/liquid extraction partitions an analyte between two immiscible phases, such as an organic solvent and an aqueous phase. When an aqueous phase contains the analyte it is extracted into the immiscible organic solvent by placing the two phases into contact. Extraction is enhanced by mixing. A relatively large volume of solvent (typically greater than 100 mL) is necessary to carry out the extraction. Partitioning of a compound between the solution solvent and extractant solvent is governed by the distribution constant, K, and the phase ratio, r (The ratio of the quantity of the solvent to that of the other phase). An example of such an extraction would be EPA test method SW846 3510 which specifies that one liter of aqueous sample should be serially extracted with 350 mL of methylene chloride. When the entire procedure is considered, a total of 500 mL of solvent is used for each sample. The solvent extract must be evaporated to reduce its volume to between 1 and 2 mL for placement into an autosampler vial prior to analysis.

Solid phase extraction (SPE) is often used to extract a sample prior to analysis by chromatography. SPE uses silica particles with an organic layer covalently attached to the surface of the particles. The silica particles are packed into a tube or disc, such as a polyethylene syringe barrel. The sample is then prepared and an analyte extracted by passing the sample through the solid sorbent. The analyte is then desorbed from the SPE media by solvent extraction. An example of such an extraction is EPA test method SW846 3535 which utilizes one liter of sample but requires approximately 50 mL of solvents. The solvent extract must be evaporated to reduce its volume to between 1 and 2 mL for placement into an autosampler vial prior to analysis.

It is known in the art to use a sorbent to extract an analyte from a solution. The analyte is later extracted from the sorbent by thermal desorption or by back extracting with a small amount of organic solvent. Sorption materials are usually homogenous, non-porous materials that are above their glass transition point ($T_g$) and in which the analyte can dissolve. The sample may be removed for analysis by thermal desorption or solvent extraction.

Solid phase microextraction (SPME) is an extraction technique wherein a fiber is coated with a sorbent layer. The coating may be a polysiloxane or other immobilized sorbent. The fiber is immersed in a liquid or exposed to its headspace during which time the analyte is retained. The fiber may then be inserted into a gas chromatograph injection port for analysis where it is thermally desorbed or may be back extracted with a suitable solvent. SPME is not accepted for EPA test methods.

Stir-bar sorptive extraction (SBSE) is used primarily for direct mode sampling. SBSE utilizes a thick sorbent coating on a magnetic bar stirrer that stirs the sample for a predetermined amount of time during which time the analyte partitions between the stir-bar sorbent and the sample. After extraction, the stir-bar is removed and the analyte is thermally desorbed to the injection port of a gas chromatograph.

Examples of the prior art follow:

U.S. Pat. No. 5,595,653 issued to Good et al. on Jan. 21, 1997 discloses an apparatus for extracting an analyte from a liquid sample. The apparatus comprises a microcolumn having a microparticulate media sandwiched between two compression layers. The compression layers are preferably a binder-free glass fiber, held in the microcolumn by upper and lower polypropylene mesh.

U.S. Pat. No. 5,635,060 issued to Hagen et al. on Jun. 3, 1997 discloses a solid phase extraction or chromatographic medium. The medium comprises a porous nonwoven fibrous matrix comprising at least one of polytetrafluoroethylene and blown microfibers, and sorptive or reactive hydrophobic siliceous molecular sieve particulates enmeshed in the matrix.

U.S. Pat. No. 5,911,883 issued to Anderson on Jun. 15, 1999 discloses a solid phase extraction article having a porous, particle loaded, fibrous sheet material spiral-wrapped around its axis is provided. The sheet material is wound around itself to provide multiple layers of sheet material, each layer of sheet material being spaced from each adjacent layer of sheet material.

U.S. Pat. No. 5,897,779 issued to Wisted et al. on Apr. 27, 1999 discloses a cartridge device for removing an analyte from a fluid. The cartridge comprises a hollow core, a sheet composite comprising a particulate-loaded porous membrane and, optionally, at least one reinforcing spacer sheet. The particulate is capable of binding the analyte and the sheet composite is formed into a spiral configuration about the core.

U.S. Pat. Nos. 5,415,779 and 5,595,649 both issued to Markell et al. on May 16, 1995 and Jan. 21, 1997, respectively, disclose a particle loaded, porous, fibrous compressed or fused article for separations and purifications. The article comprises a nonwoven fibrous polymeric web, which preferably is thermoplastic, melt-extrudable, and pressure-fusible blown microfibrous web, and sorptive particles enmeshed in the web.

U.S. Pat. No. 5,472,600 issued to Ellefson et al. on Dec. 5, 1995 discloses a gradient density filter made from sheets of blown polypropylene microfibers where the microfibers of at least one of the sheets have an effective fiber diameter less than that of the other sheets.

U.S. Pat. No. 5,403,489 issued to Hagen et al. on Apr. 4, 1995 discloses a method and apparatus for performing solid phase extraction (SPE) on a fluid that contains solubles and suspended solids. The apparatus includes a conduit, a SPE medium located in the conduit, and a fluid flow direction altering mechanism or a SPE rotating mechanism.

U.S. Pat. No. 5,391,298 issued to Pieper et al. on Feb. 21, 1995 discloses an apparatus that can be used to perform a solid phase extraction under pressurized conditions. The apparatus includes a pressurizable housing with an inlet tube that can communicate with a pump, which feeds a liquid to the housing under positive pressure. A disk assembly includes fluid-permeable, porous sheets on opposite sides of an SPE membrane.

U.S. Pat. No. 5,279,742 issued to Markel et al. on Jan. 18, 1994, reissued as U.S. Pat. No. Re. 36,811 on Aug. 8, 2000 discloses a method for isolating an environmentally hazardous organic contaminant from a fluid utilizing a solid phase extraction medium. The medium comprises a PTFE fibril matrix, and sorptive particles enmeshed in the matrix. The separations can be efficiently performed in a stacked disk format.

U.S. Pat. No. 5,691,206, issued to Pawliszyn on Nov. 25, 1997 discloses a device for carrying out solid phase microextraction. The device is a fiber, solid or hollow, contained in a syringe. The syringe has a barrel, a plunger slidable within the barrel and a hollow needle extending from the end of the barrel opposite the plunger. The needle contains the fiber. When the plunger is depressed, the fiber extends beyond a free end of the needle and when the plunger is in a withdrawn position the fiber is located within the needle. To collect a sample, the needle is inserted through a septum in a bottle containing the sample and the fiber is extended into the sample. After a predetermined amount of time, the fiber is returned to the needle and the syringe is withdrawn from the bottle. The sample is analyzed by inserting the needle through a septum in a gas injection port of a gas chromatograph and extending the fiber.

U.S. Pat. No. 5,565,622, issued to Murphy on Oct. 15, 1996 discloses a simplified method for solid phase extraction of components of interest from a sample. A syringe is used in which the inner surface of the cannula or needle is at least partially coated with a stationary phase such that aspirating the sample into the needle results in adsorption of the components of interest into the stationary phase. Aspiration of a solvent may be employed for removing the components of interest from the stationary phase for direct injection into a chromatographic instrument, or the components of interest may be removed by thermal desorption, wherein the needle is placed in the injection port of the chromatographic instrument and heated.

U.S. Pat. Application Pub. No. US 2002/0105923, applied for by Malik, published on Oct. 17, 2002 discloses a method of preconcentrating trace analytes by extracting polar and non-polar analytes through a sol-gel coating. The sol-gel coating is either disposed on the inner surface of the capillary tube or disposed within the tube as a monolithic bed.

It would be an improvement to the art to have a device in which the extraction may be performed and the analyte conveniently and transportably stored for later analysis.

BRIEF SUMMARY OF THE INVENTION

The present invention comprises a device and method for performing direct vial extraction.

Accordingly, the objects of my invention are to provide, inter alia, a single step solid phase extraction system that:
  minimizes the amount of solvent used;
  minimizes the amount of labor required to perform an extraction;
  minimizes glassware;
  allows samples to be archived;
  allows extraction to be performed at the sampling site rather than the laboratory;
  allows the extract to be subjected to replicate analysis;
  allows the use of gas or liquid chromatography autosamplers;
  allows the use of disposable sample vials;
  has greater reproducibility than solid phase micro extraction;
  reduces or eliminates sample cross contamination; and
  does not require expensive thermal desorption equipment.

This invention is a sorption vial that can be used for the extraction of a sample, or analyte, from a sample matrix and a method of using the sorption vial to perform the extraction. Preferably, the sorption vial has a conically-shaped interior bottom surface coated with sorptive material. An adapter may retain the sorption vial in a fixed position within a larger sample vessel such that the sorptive coating is exposed to a sample or its headspace. After partitioning of the sample in to the sorptive material, the sorption vial may be removed from the sample vessel. An elution solvent is used to extract the analytes from the sorptive coating, which is then sealed and transported to a location for further testing. Alternatively, the sorption vial may be used directly to receive the sample and perform the extraction without using the larger sample vessel.

DESCRIPTION OF THE INVENTION

Figure 1:
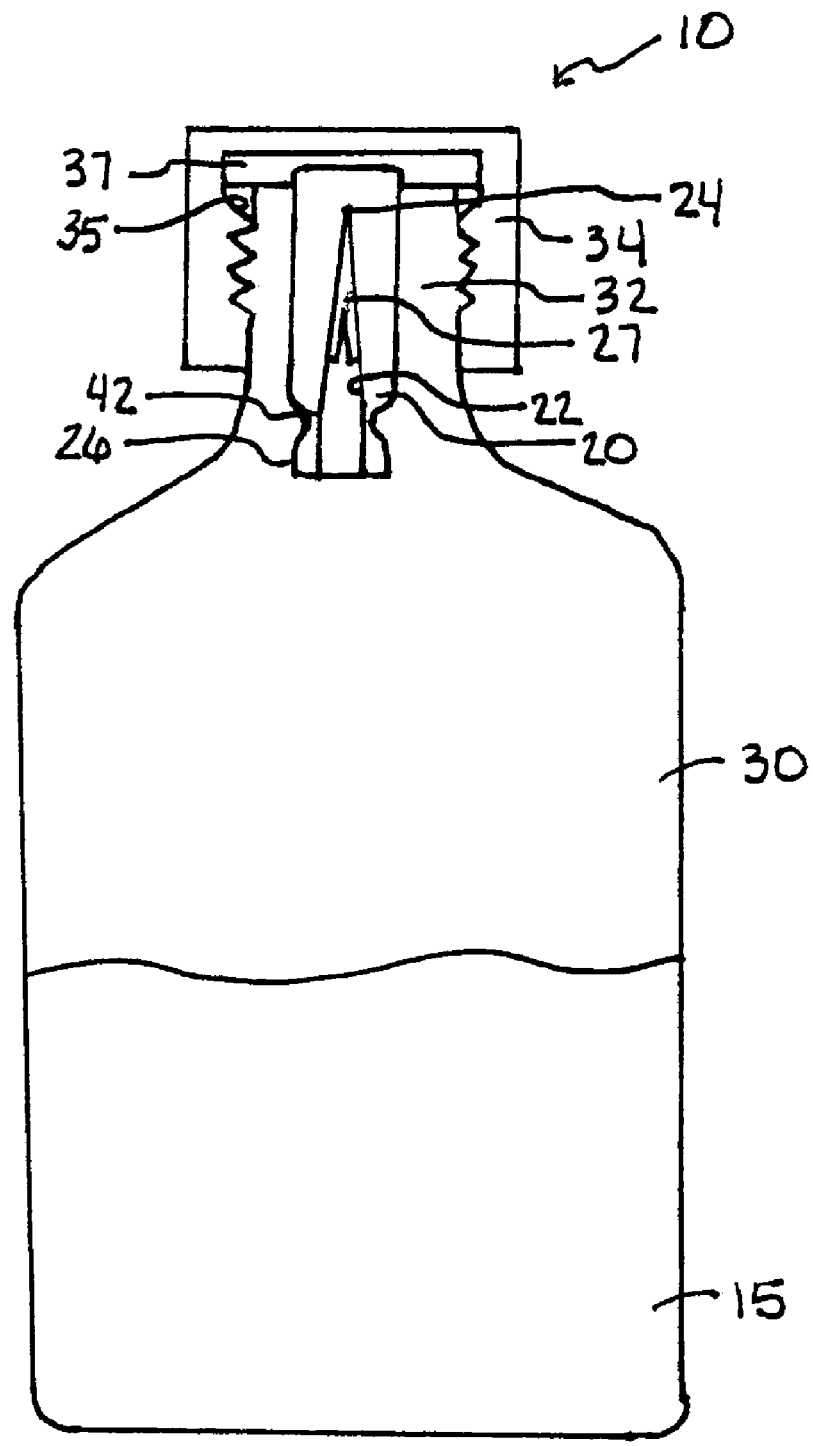
FIG. 1 is a cross-sectional view of a sample vessel with a sorption vial.

Referring to FIG. 1, the preferred embodiment of the surface sorbent micro extraction (SSME) assembly is depicted as 10. SSME assembly 10 comprises a sorption vial 20 and a sample vessel 30.

Figure 2:
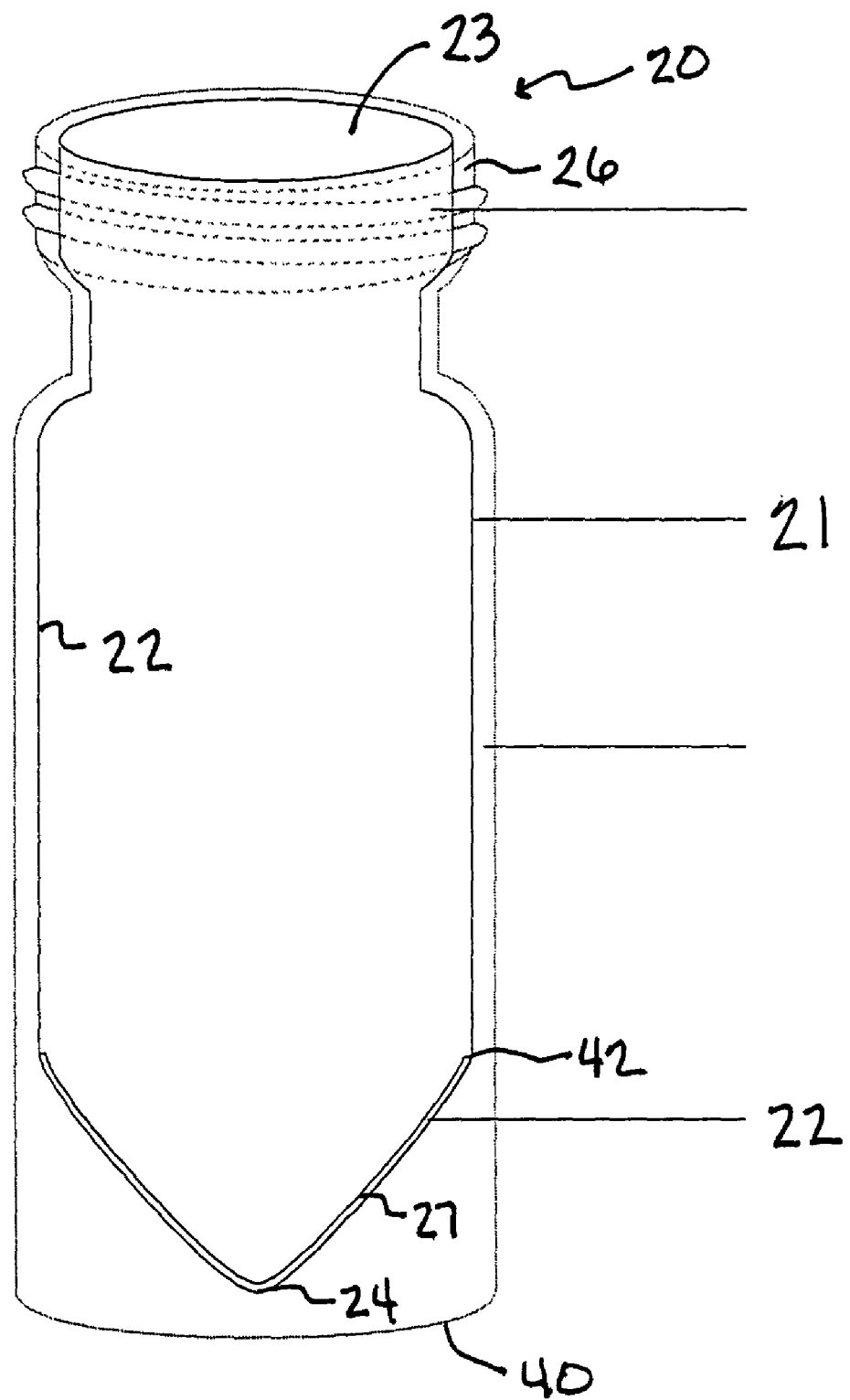
FIG. 2 is a perspective view of the preferred embodiment of a sorption vial.

Referring to FIGS. 1 and 2, sorption vial 20 is made from a rigid, nonreactive material, such as silica glass. In the preferred embodiment, sorption vial 20 has a cylindrically-shaped interior wall 21 with a conically-shaped bottom surface 22. Sorption vial 20 also has a vial base 40 and a vial neck 26 through which there is an opening 23 to interior surface 22. Bottom surface 22 is oriented such that the vertex 24 of the conical bottom surface 22 is proximate vial base 40 while the directrix 42 is contiguous with interior wall 21.

Figure 4:
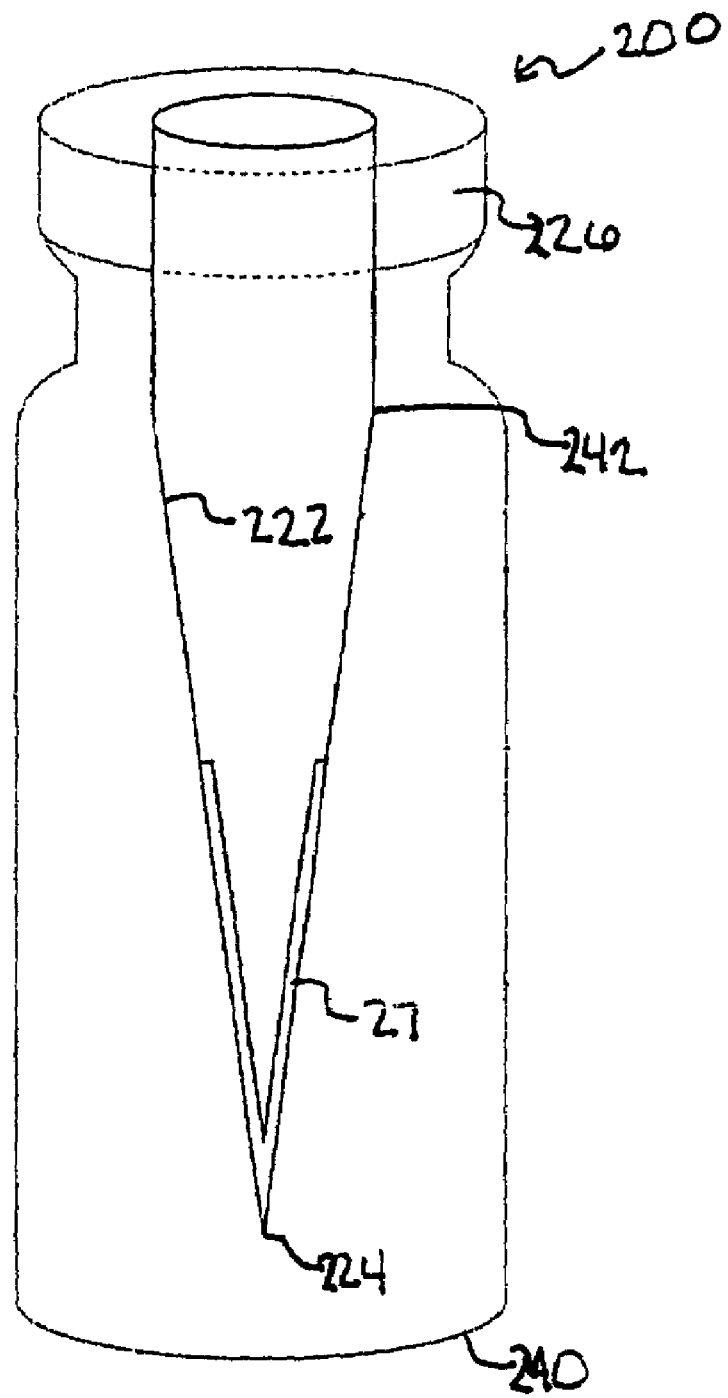
FIG. 4 is a perspective view of an alternative embodiment of a sorption vial.

An alternative embodiment of sorption vial 20 is shown in FIG. 4 as sorption vial 200. Interior wall 222 is conically shaped. Alternative interior wall 222 is oriented such that the vertex 224 of the conical interior wall 222 is proximate vial base 240 while the directrix 242 is proximate vial neck 226.

Figure 3:
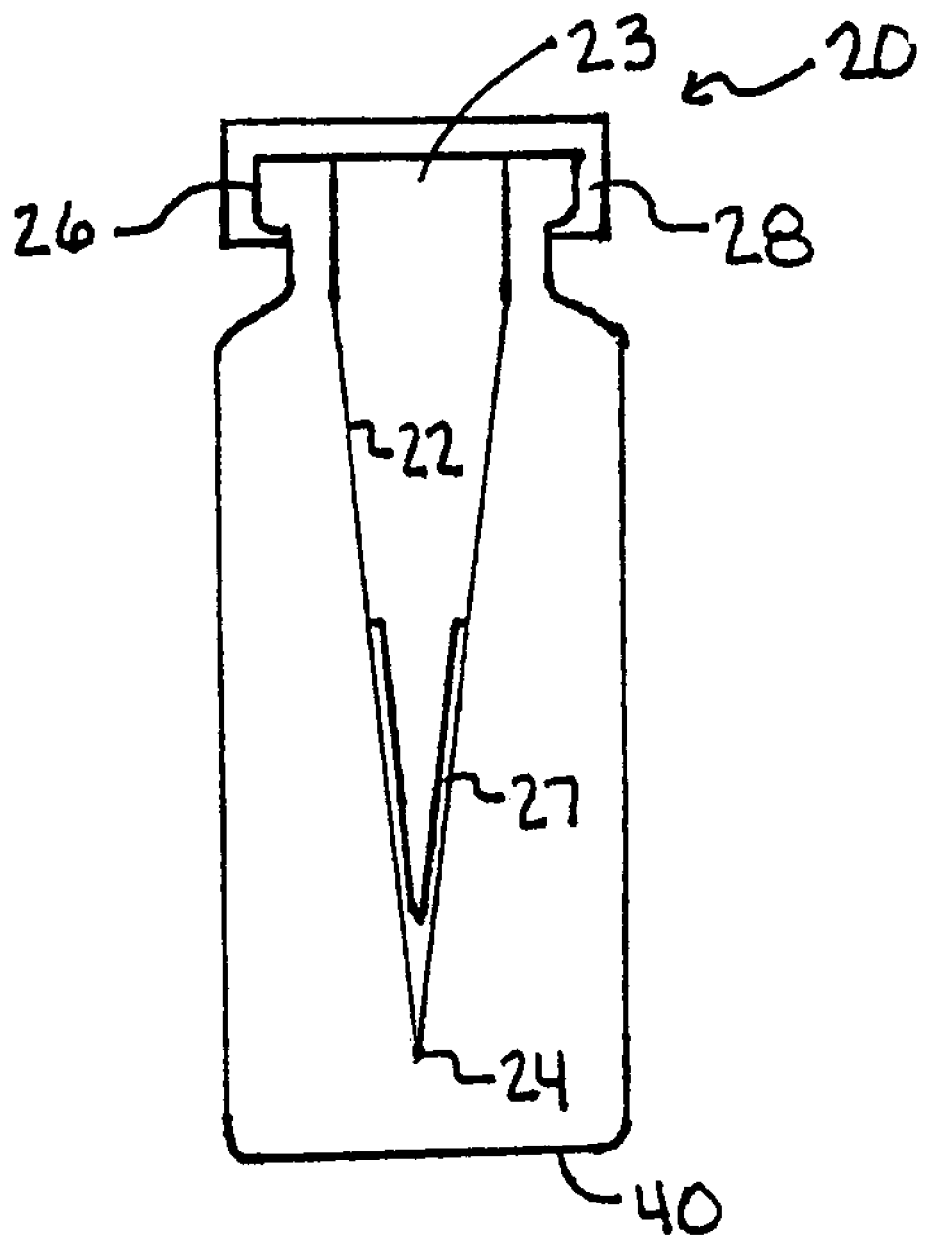
FIG. 3 is a cross-sectional view of a sorption vial with a vial cap.

It is known in the art that vials need a means for closure. It is also known in the art that autosamplers require a means by which they may grasp the vial. Referring to FIGS. 2 and 3, vial neck 26 is an example of a means known in the art by which vials may be sealed and provide a shape suitable to autosamplers. In this example vial neck is formed such that a vial cap 28 may be placed over opening 23 to seal sorption vial 20 after a sample 15 (shown in FIG. 1) containing the analyte to be extracted is exposed to interior surface 22. Vial cap 28 may be any type of cap including a screw-on cap, a crimp cap, or a plug, so long as vial cap 28 is leak-proof.

A sorptive coating 27 is applied proximate the vertex 24 of interior surface 22. When interior surface 22 is cylindrical rather than conical, sorptive coating 27 may be applied on the cylinder interior wall or the flat or conical bottom surface or both.

In the preferred embodiment, the sorptive coating 27 is a hydrophobic coating, such as an immobilized polysiloxane, for example polydimethylsiloxane (PDMS), which contains only methyl functional groups. The name "siloxane" is based on the Si—O—Si unit and has found acceptance in scientific nomenclature. Polysiloxanes are polymers with repeating siloxane units. Each repeating siloxane unit contains two functional groups attached (e.g. dimethyl) which may, or may not, be of the same type of functional group. A functional group is an atom or combination of atoms which gives a polymer its distinctive and characteristic chemistry. A polysiloxane of 50 repeating units would therefore have 100 methyl groups, whereas a siloxane unit with two different types of groups such as phenymethyl would have 50 of each "type" in the polysiloxane.

It is known in the art that immobilized polysiloxanes that contain other types of functional groups, may be used as sorbents. These include immobilized polysiloxanes containing phenyl or trifluoropropyl functional groups. Examples of these polysiloxanes include diphenylsiloxane-dimethylsiloxane copolymers and trifluoropropylmethylsiloxanes. For more selective sorption applications the immobilized polysiloxane may contain other types of functional groups including alkyl, alkenyl, alkynyl, aryl, alkylaryl, alkenylaryl, alkynylaryl, haloalkyl or haloaryl. A polysiloxane may contain said types of functional groups in any combination. The selection of the type of functional groups permits the partitioning of a particular analyte or analyes from the sample The polysiloxane coating may be a polymer, a copolymer or a combination of polymers.

Alternatively, sorptive coating 27 may be (1) a porous layer, such as a derivatized etched surface, (2) other immobilized polymers that are above their glass transition temperatures such as poly butadiene, (3) an immobilized porous polymer, such as divinylbenzene, ethyleneglycoldimethacrylate, and copolymers of divinylbenzene and ethyleneglycoldimethacrylate, polyethyleneimine, acrylonitrile, n-vinyl-2-pyrollidinone or 4-vinyl-pyridine, (4) a sol gel or (5) an immobilized adsorbent such as graphatized carbon black. Sorptive coating 27 may be any one of the coatings described or a combination of two or more of the alternative coatings. The selection of the coating or coatings by one skilled in the art is dependent upon the analyte or analytes to be partitioned from sample.

Referring again to FIG. 1, sample vessel 30 is used to collect sample 15 from which the analyte is to be extracted. Sample vessel 30 is made from a rigid, nonreactive material, such as silica glass, and has a mouth 32. A cap 34 is used to close the sample vessel 30 at mouth 32. Cap 34 has an interior surface 35, within which base 40 of sorption vial 20 selectively attaches.

When sample vessel 30 is closed with sorption vial 20 attached to cap 34, opening 23 faces toward sample 15. When sample vessel 30 is sealed and inverted, contained liquid sample 15 contacts sorptive coating 27. Alternatively, sample vessel 30 may be maintained in an upright position with sorption vial 20 exposed to the head space of a collected sample. The analyte within sample 15 is partitioned between sample 15 and sorptive coating 27. The small surface area of interior surface 22 allows for rapid exchange of a vapor or liquid as well as for desorption by the least volume of solvent. Sorption vial 20 may then be removed from cap 34, desorbed by a suitable solvent, sealed and stored or transported from the test collection site to a location for testing.

The extraction process comprises placing a sample in sample vessel 30. Sorption vial 20 is then attached to cap 34 or cap liner 37 and sample vessel 30 is sealed. As previously explained, sorption vial 20 is attached within sample vessel 30 such that interior surface 22 will be exposed to samples within sample vessel 30 or the headspace of such samples. Sample vessel 30 may be agitated for a predetermined period of time to allow equilibrated partitioning. Sorption vial 20 is removed from sample vessel 30. A predetermined amount of elution solvent (not shown) is measured into sorption vial 20, and sorption vial 20 is sealed. The collected sample may be analyzed by gas chromatography, high performance liquid chromatography or other analytical instruments. Alternatively, the collected sample may be stored for future analysis.

In certain cases, such as when a sample has a high viscosity, agitation is not desired. In such cases, collection may take place by exposing sorption vial 20 to the headspace of sample 15. Sample vessel 30 may be stirred for a predetermined amount of time to enhance equilibrated partitioning. Partitioning takes place between sample 15, it's headspace and the sorptive coating 27.

In some cases the volume of sample is equal to or less than the volume of sorption vial 20. In this case sample vial 20 receives a similar sorptive coating 20 such as PDMS. Sorption vial 20 is then filled with the solution containing analytes to be extracted thus eliminating the need for the sample vessel 30. A mechanical shaker (not shown) is used to agitate sorption vial 20 and to assist in bringing the partitioning to equilibrium. Sorption vial 20 is emptied and a predetermined amount of elution solvent (not shown) is measured into sorption vial 20. A vial cap 28 seals sorption vial 20. The contents (not shown) of sorption vial 20 may then be sampled as required. The preferred embodiment of sample vial 20, shown in FIG. 2, is particularly well suited for this method.

The foregoing disclosure and description of the invention is illustrative and explanatory thereof. Various changes in the details of the illustrated construction may be made within the scope of the appended claims without departing from the spirit of the invention. The present invention should only be limited by the following claims and their legal equivalents.

What is claimed is:

1. A device for the collection and extraction of at least one analyte within a sample, said device comprising:
    a sorption vial including an interior surface, an opening to said interior surface and a closed vial base;
    a sorptive coating on said interior surface;
    a sample vessel for collecting said sample;
    a cap for closing said sample vessel; and
    said vial base removably attached to said cap, said cap retaining said sorption vial within said sample vessel during said collection and said extraction.

2. The device of claim 1, further comprising:
    said interior surface having a conical shape;
    said conically-shaped interior surface having a vertex and a directrix;

said vertex proximate said vial base;
said directrix facing said opening.

3. The device of claim 1, further comprising:
said interior surface including an interior wall and an interior base;
said interior base having a conical shape;
said conically-shaped interior base having a vertex and a directrix;
said vertex proximate said vial base;
said directrix contiguous with said interior wall; and
said sorptive coating covering said conically-shaped interior base.

4. The device of claim 3, wherein said sorption vial comprises silica glass.

5. The device of claim 3, further comprising:
said sorptive coating comprising an immobilized polysiloxane polymer having one type of functional group selected from the group consisting of alkyl, alkenyl, alkynyl, aryl, alkylaryl, alkenylaryl, alkynylaryl, haloalkyl and haloaryl.

6. The device of claim 3, further comprising:
said sorptive coating comprising an immobilized polysiloxane polymer having at least two types of functional groups selected from the group consisting of alkyl, alkenyl, alkynyl, aryl, alkylaryl, alkenylaryl, alkynylaryl, haloalkyl and haloaryl.

7. The device of claim 3, wherein said sorptive coating comprises an immobilized porous polymer.

8. The device of claim 7, wherein said immobilized porous polymer is selected from the group consisting of: divinylbenzene, ethyleneglycoldimethacrylate, polyethyleneimine, acrylonitrile, n-vinyl-2-pyrollidinone, and 4-vinyl-pyridine.

9. The device of claim 3, wherein said sorptive coating comprises a sol gel coating.

10. The device of claim 3, wherein said sorptive coating is a polymer existing above its glass transition temperature.

11. The device of claim 3, further comprising:
a vial cap for sealing said sorption vial; and
said vial cap covering said opening.

12. A device for the collection and extraction of at least one analyte within a sample, said device comprising:
a sorption vial including an interior wall, an interior base, an opening to said interior wall and said interior base and a vial base;
said interior base having a conical shape;
said conically-shaped interior base having a vertex and a directrix;
said vertex proximate said vial base;
said directrix contiguous with said interior wall;
a sorptive coating on said conically-shaped interior base;
a sample vessel for collecting said sample;
a cap for closing said sample vessel;
said vial base removably attached to said cap;
a vial cap for sealing said sorption vial; and
said vial cap covering said opening.

13. The device of claim 12, further comprising:
said sorptive coating comprising an immobilized polysiloxane polymer having one type of functional group selected from the group consisting of alkyl, alkenyl, alkynyl, aryl, alkylaryl, alkenylaryl, alkynylaryl, haloalkyl and haloaryl.

14. The device of claim 12, further comprising:
said sorptive coating comprising an immobilized polysiloxane polymer having at least two types of functional groups selected from the group consisting of alkyl, alkenyl, alkynyl, aryl, alkylaryl, alkenylaryl, alkynylaryl, haloalkyl and haloaryl.

15. The device of claim 12, wherein said sorptive coating comprises an immobilized porous polymer.

16. The device of claim 15, wherein said immobilized porous polymer is selected from the group consisting of: divinylbenzene, ethyleneglycoldimethacrylate, polyethyleneimine, acrylonitrile, n-vinyl-2-pyrollidinone, and 4-vinyl-pyridine.

17. The device of claim 12, wherein said sorptive coating comprises a sol gel coating.

18. The device of claim 12, wherein said sorptive coating is a polymer existing above its glass transition temperature.

19. A method for performing direct vial extraction of analytes from a sample utilizing a sorption vial and a sample vessel, said sorption vial including a closed vial base, a vial interior, and a vial opening, said method comprising:
coating said vial interior with a sorptive material;
removably attaching said closed vial base to a cap;
collecting a liquid sample in said sample vessel;
closing said sample vessel with said cap, said cap retaining said sorption vial within said sample vessel;
exposing said liquid sample to said sorptive coating;
opening said sample vessel;
removing said sorption vial from said cap;
adding a solvent to said sorption vial; and
sealing said sorption vial with a vial cap.

20. The method of claim 19 wherein said exposing step comprises agitating said sample vessel.

21. The method of claim 19 wherein said exposing step comprises subjecting said sorption vial to a headspace above said sample.

22. The method of claim 19 wherein said vial interior including a conically-shaped bottom surface; and
said coating step including coating said conically-shaped bottom surface with said sorptive coating.

* * * * *